United States Patent [19]

Cané

[11] Patent Number: 4,662,872

[45] Date of Patent: * May 5, 1987

[54] INSULIN ADMINISTRATING APPARATUS

[76] Inventor: Mario Cané, Via Allegri 11, Collegno (prov. Torino), Italy

[*] Notice: The portion of the term of this patent subsequent to Apr. 5, 2003 has been disclaimed.

[21] Appl. No.: 627,151

[22] Filed: Jul. 2, 1984

Related U.S. Application Data

[63] Continuation-in-part of Ser. No. 393,151, Jun. 28, 1982, abandoned.

[30] Foreign Application Priority Data

Jul. 9, 1981 [IT] Italy ............................... 67951 A/81

[51] Int. Cl.⁴ ............................................... A61M 5/20
[52] U.S. Cl. ............................ 604/151; 128/DIG. 1; 310/168; 604/154
[58] Field of Search ................ 604/154, 155, 67, 151; 128/DIG. 12, DIG. 1; 310/168, 170

[56] References Cited

U.S. PATENT DOCUMENTS

| | | | |
|---|---|---|---|
| 3,132,337 | 5/1964 | Martin | 310/170 |
| 3,930,201 | 12/1975 | Ackermann et al. | 310/168 |
| 4,191,187 | 3/1980 | Wright | 128/DIG. 1 |
| 4,282,872 | 8/1981 | Frangtzki et al. | 604/151 |
| 4,305,072 | 12/1981 | Makita | 310/168 |

Primary Examiner—Edward M. Coven
Attorney, Agent, or Firm—Guido Modiano; Albert Josif

[57] ABSTRACT

The apparatus comprises an auxiliary pushbutton control for delivering insulin doses ahead of meals, an electric motor for producing a minimal angular advance movement of the administering syringe plunger pusher and programmable circuitry for multiplexing the minimal advance movements and providing programmed sequences of the multiplexed minimal advance movements at each operation of the pushbutton control.

3 Claims, 3 Drawing Figures

INSULIN ADMINISTRATING APPARATUS

This is a continuation-in-part of patent application Ser. No. 393,151 filed on June 28, 1982, now abandoned.

BACKGROUND OF THE INVENTION

This invention relates to insulin administrating apparatus of the type which comprises a portable proportioning dispenser with a syringe for injecting the remedy into the patient through a needle being steadily introduced subcutaneously, and means adapted to produce a programmed and controlled forward movement of the syringe plunger.

Known are apparatus of this type, wherein the syringe plunger forward movement is produced by means of a pusher with a nut screw threaded seat wherein is engaged a matching threaded shaft rotatively driven, at programmed intervals, by an electric motor operated through an electronic control circuit.

The dosage occurs by controlling or adjusting the shaft rotation by subdividing it into basic angular ranges of preset amplitude, e.g. 90°. Moreover, upon completion of each angular rotation, the rotary movement is discontinued and resumed after a programmable time lapse which establishes the dosage intervals.

The power supply to the motor is interrupted by the action of sensors sensing the shaft angular position and reset by an electronic timer comprising a driving oscillator and divider which sends the enabling command to the power supply as a preset number of pulses from the oscillator are counted thereby by varying the oscillator frequency, the rate of operation of the timer is changed. In general, known apparatus of the type specified above comprise two timing rates produced by corresponding oscillator frequencies, or by respective driving oscillators, and means for programming the time duration of the higher timing rate.

The known apparatus hereinabove specified have given satisfactory results but have some drawbacks resulting from the necessity of discontinuous insulin administrations in relation to particular situations of the patient's metabolic cycle.

As in known, in fact, with diabetic patients the necessity of administrating insulin grows with the assumption of meals and the amount varies proportionally with the magnitude of the meal itself.

A prevailing medical trend recommends the assumption of the extraordinary dose ahead of meals in a single solution. For this purpose the prior apparatus of the type specified are provided with devices for advancing the syringe pusher which are controlled each time by the patient for the administration of the extraordinary dose. A proposed device comprises a manually controlled, suitably scaled, screw which acts on the threaded shaft to produce the forward movement of the syringe pusher while excluding the motor action. Another device avails itself of a push-button which, when actuated directly by the patient, activates the motor; for each actuation of the push-button there corresponds a basic angular rotation range of the pusher-moving threaded shaft.

Both these systems have proved to be impractical but above all unreliable in relation to the excessive care that the patient is to pay in controlling the screw, or respectively the pushbutton, to achieve a precise delivery of the prescribed dose.

In particular with the motor pushbutton actuating system, since each actuation results in a basic angular rotation range, the number of the pushbutton actuations may be very high, e.g. 20 actuations. It will be appreciated that such a circumstance may originate even appreciable counting errors and be inconvenient and annoying for the patient.

SUMMARY OF THE INVENTION

This invention is essentially directed to eliminate these drawbacks.

According to one aspect of the invention this object is achieved by an insulin administrating apparatus with a pusher for moving forward the administration syringe plunger driven by a driven shaft driven by an electric motor with timed forward movement, characterized in that it comprises means for establishing a minimal angular advance movement of said driveshaft and means for programmably multiplexing said minimal advance movements and producing programmed sequences of said multiplexed minimal advance movements at each actuation of a pushbutton pre-arranged for delivering extraordinary doses ahead of meals.

More specifically the invention is based on the concept of establishing a minimal angular advance movement for the driveshaft of the pusher of the syringe, multiplexing said minimal advance movements through a prior programming and producing the programmed sequence of said multiplexed minimal advance movements at each actuation of a pushbutton pre-arranged for dispensing extraordinary doses. For a given pitch of the thread of the driveshaft, the diameter of the syringe being known, each minimal advance movement is selected to be equal to one unit or unit submultiple of insuline "U.I.". Thus, the prescribed extraordinary dose, expressed in units, will be delivered by depressing the pushbutton for a number of times equal to the number of prescribed units divided by the number of units multiplexed by programming. Thus, for example, if the prescribed extraordinary dose is 10 units insulin the unitary advance movement is 0.5 units and 5 advance movements are programmed in multiple sequence, and each actuation of the pushbutton will deliver 2.5 units and the prescribed dose will be dispensed by depressing the pushbutton n=10/2.5=4 times. The base concept of the invention is implemented, therefore, by providing—in an administrating apparatus as specified—an auxiliary supply circuit for the advance movement motor with a manual actuation pushbutton associated with self-holding means and a further programmable frequency oscillator-divider associated with a detector of the angular displacements of the actuating shaft of the syringe pusher; the oscillator-divider, activated by the pushbutton being adapted to carry out the ratio between the frequency of the local oscillator and the pulses of the displacement detector to emit a manual pushbutton deactivating pulse as the number of cycles of the oscillator, contained in the pulses of the displacement detector, reaches the fixed ratio of the frequency divider. It will be then readily appreciated that for variations in the oscillator frequency there correspond variations in the angular rotation range of the driveshaft read by said displacement detector.

BRIEF DESCRIPTION OF THE DRAWING

The invention will be next described in detail with reference to the accompanying drawings, given herein by way of example and not of limitation, and where.

DESCRIPTION OF THE PREFERRED EMBODIMENTS

Figure 1:
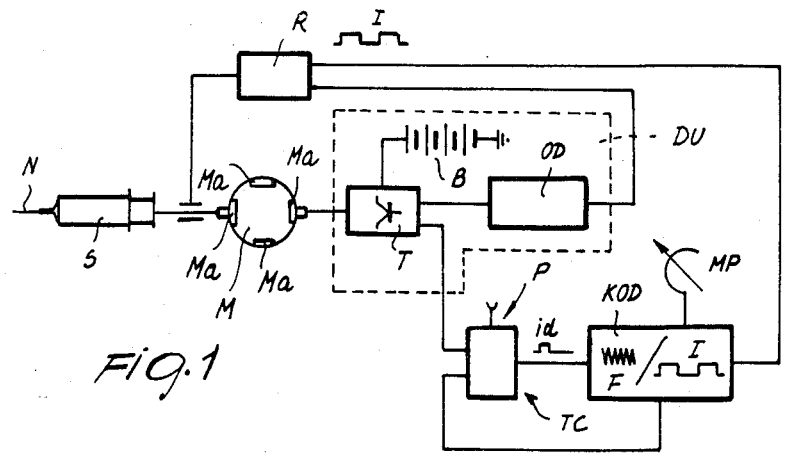
FIG. 1 is a block diagram of the motor supply circuit of the improved apparatus according to this invention.

In the drawings M designates a dc motor which, through a threaded shaft engaging the nut screw of a pusher, drives, in a manner known per se, the plunger of an administrating syringe S having a needle N. The shaft has a plurality of permanent magnets, preferaly four, schematically indicated at Ma arranged at 90°, associated with interrupting means responding to the field produced by said magnets, e.g. a conventional switch of the reed type R, the magnet Ma and cooperating reed switch R constituting a detector of the angular movements of the shaft. The reed switch R, due to the passage of the magnets Ma in proximity thereof, generates in a per se known manner, a sequence of rectangular pulses I fed to a motor driving unit DU and to a control circuit KOD. The driving unit DU, powering the motor M, comprises a battery B, a control group T comprising a transistor or other equivalent means, with on/off switch functions and an oscillator-divider OD-. The conductive state of the transistor or control group T is controlled in a manner known per se by the oscillator-divider OD with timer functions which, when ever activated by a constant pulse I from the reed switch R, sends to the base of said transistor a train of activating pulses rated at a period depending on the oscillator frequency for a preset time. Therefore, the control group T feeds the motor M with electrical signals from the power unit or battery B to energize the motor to produce a predetermined unitary advance movement of the plunger for each pulse I. The motor operates, therefore, intermittently producing stepped angular movements of the shaft, which drives the syringe pusher, the step rate depending on the oscillator frequency. It should be noted that the frequency of the oscillator can be varied in a continuous manner to produce corresponding angular step rates of the shaft.

According to this invention the conductive state of the transistor T is further controlled by a control circuit comprising a manual pushbutton P, an electronic toggle circuit TC and a second oscillator-divider KOD. The pushbutton P, when actuated, sets the toggle circuit TC, which is of the type having two different stable states, such as a flip-flop or a relais. Such toggle circuit responds to or is reset by a de-activating or inhibition pulse produced by the second oscillator-divider KOD which, also activated by the pushbutton P, carries out the ratio between the frequency F of its local oscillator and the number of pulses I received from the switch R and emits a pushbutton de-activating signal id as the number of cycles of the oscillator frequency contained in the pulses (of constant duration) of the detector reaches the dividing ratio of the oscillator-divider device. Thus, for example, making reference to FIG. 2, if the dividing ratio Y preset for the oscillator-divider KOD is 100/1, that is it emits at the output a de-activating pulse id every 100 cycles of the local oscillaotr, assuming that the frequency F of the oscillator is selected such that 20 cycles are counted for each pulse I of the detector, then the pushbutton de-activating pulse will be emitted after 5 pulses I of the position detector. It will be readily appreciated that by varying the frequency F of the local oscillator, through a programming knob MP, the number of pulses I and pulse fractions of the position detector required to produce the de-activating pulse id is varied. Consequently, the time interval between the activation of the toggle circuit TC by the pushbutton P and the de-activating pulse id varies as well as the angular movement range of the driveshaft, read by the displacement detector, and hence the amount of the dispensed administration units. In practice, if in the above example the frequency F of the local oscillator were increased, more than 20 cycles of the local oscillator would be counted for each pulse I and, therefore, a lower amount of insulin were dispensed for each actuation of the pushbutton P.

Figure 2:
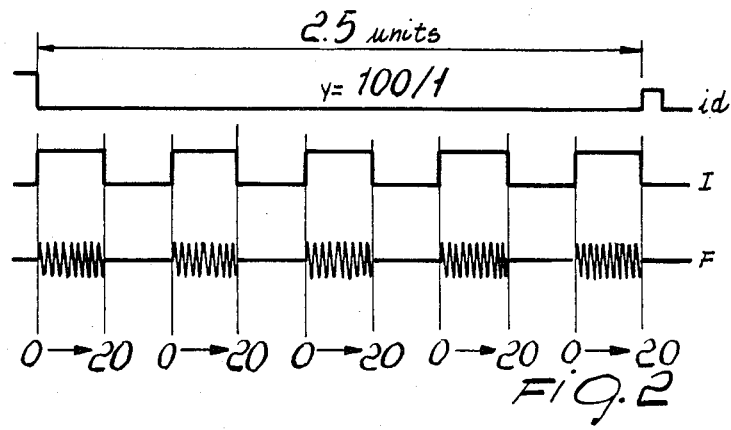
FIG. 2 is an explanatory diagram of the operation of said further oscillator-divider.

The programming according to the diagram of FIG. 2 relates to the example just described wherein the unitary advance movement, corresponding to an angular movement range of 45° of the driveshaft and equal to 0.5 units insulin "U.I." and wherein programmed in multiple sequence are 5 advance movements for a total delivery of 2.5 units per actuation of the pushbutton P. The de-activating pulse id advantageously energizes an acoustic signaller, which warns of the effected delivery, possibly with a counting signalling. The oscillator-divider KOD is advantageously comprised of a shift register associated with an oscillator (Clock) at a programmable frequency. By keeping unvaried the unitary advance movement it is possible to vary the dose dispensed at each forward movement of the pusher by varying the frequency F with the programming knob MP. For example by selecting a frequency F such that fifty cycles of the local oscillator are counted in one pulse I of the position detector (i.e. the de-activating pulse id, emitted after 100 pulses of the local oscillator, occurs after two pulses I of the detector R), each actuation of the pushbutton P will produce the total delivery of one unit insulin. The programming knob is preferably calibrated in units of dispensed insulin (U.I.).

Figure 3:
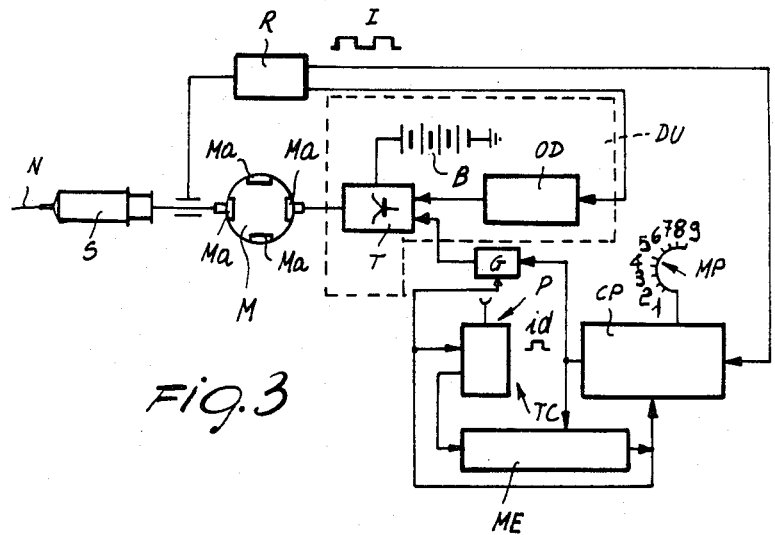
FIG. 3 is a block diagram of another embodiment of the motor supply circuit of the improved apparatus according to the invention.

FIG. 3 shows another embodiment of the apparatus according to the invention, which has been designed, in order to avoid the necessity of waiting the delivery of the programmed units of insulin before the actuation of the pushbutton for the delivery of subsequent programmed units. The embodiment shown in FIG. 3 differs from the one illustrated on FIG. 1 only with respect to the control circuit, so that the other elements of the device (which have been here indicated with the same reference numerals as in FIG. 1) will not be described hereinafter.

According to FIG. 3, the control circuit comprises a pushbutton P connected to a programmable counter CP through a toggle circuit TC and a memory ME. The programmable counter CP forming a programming unit emits an inhibition pulse id for the electronic switch T every preset number of cycles of the detector formed also here by the magnets Ma and the reed switch R. In this embodiment, the counter CP is connected to the switch T through a gate G and to the memory ME, whereas, analogously to the embodiment according to FIG. 1, the programming knob MP allows the number of pulses I of the detector necessary for producing the inhibition pulse id at the output of the counter CP to be set. The gate G is also connected to the memory ME.

The control circuit according to FIG. 3 operates as follows: firstly, the programming knob is adjusted, in order to set the desired amount of insulin to be dispensed for each actuation of the pushbutton P (this setting needs not however to be done every time), then the pushbutton is actuated a number of times corresponding to the total amount of insulin, which should be dispensed, as it will be explained in the following example. The number of actuations of the pushbutton is stored in the memory ME which, after a predeterminated delay from the last actuation, recognizes the end of the multiple actuation. Then the memory ME emits a control pulse, which is fed to the counter, to the toggle circuit TC and to the gate G so as to enable the counter and the gate and on the same time to disable the toggle, which then inhibits the actuation of the pushbutton during the functioning of the device.

When the counter has received from the reed switch R (operating in this case as a clock) the preset number of pulses, it emits at its output the inhibition pulse id, which is fed to the driving unit DU through the gate G and to the memory ME, where it produces the decrement of one unit from the number of pulses stored in the memory ME during the actuation of the pushbutton P. When the last pulse stored in the memory ME has been discharged, the memory sends a signal to the counter CP, the gate G and to the toggle circuit TC so as to disable the counter CP and the gate G and to enable the pushbutton P.

A programming example will be now described for a better comprehension of the device according to FIG. 3. Let's suppose that the extraordinary dose ahead of each meal is of ten insulin units and the minimal basal dose is of 0.5 units, if the knob MP is set on the number 5, each activation of the pushbutton will produce a delivery of 2.5 units and the prescribed dose will be delivered by actuating 10/2.5=4 times the pushbutton P. The multiple actuation of the pushbutton is effected without breaks and it is preferably accompanied with an acoustic signal, which makes easier the counting and the control of the exact storage of the pulses by the memory ME. At the end of the multiple actuation of the pushbutton, when the predetermined delay has been passed, the memory ME activates the counter, which emits as output a pulse id every five pulses I of the switch R. Preferably also the pulses id activate an acoustic indicator for controlling the administration of the insulin.

Of course, seeing that this is the principle of the invention, the implementing details and embodiments may be amply varied with respect to what is described and illustrated by way of example and not of limitation without departing from the invention scope.

I claim:

1. An insulin administrating apparatus for deliverying extraordinary doses of insulin ahead of meals, comprising:
   a infusion syringe having a needle;
   a syringe plunger sliding within said syringe;
   an electric motor having a rotating shaft connected to and driving said syringe plunger with timed forward movement;
   motor driving means having a power unit and being connected to said electric motor for feeding said motor with energizing electric signals;
   detector means for detecting the angular displacement of said motor shaft, said detector means being connected to said motor driving means and emitting a pulse sequence indicative of the angular displacement of said motor shaft;
   a repeatedly operable pushbutton for the actuation of the apparatus;
   control circuit means for enabling said motor driving means after pushbutton actuation up to completion of delivery of programmed insulin doses, said control circuit means including a toggle circuit connected to said pushbutton; memory means connected to said toggle circuit and said motor driving means for storing the number of actuations of said pushbutton, said memory means generating an enabling signal when a preset time is elapsed from a last pushbutton actuation and a de-activating pulse when said stored number has been decremented to zero; and counter means connected to said detector means, said memory means and said motor driving means for counting the number of pulses in said pulse sequence, said counter means generating an inhibition pulse after receiving a preset number of pulses, thereby, after a preset time is elapsed from the last pushbutton actuation, the enabling signal is fed to said motor driving means for enabling insulin delivery, to said counter means for enabling counting of the sequence pulses and to said toggle circuit for inhibiting further actuations of said pushbutton, said counting means generates said inhibition pulse for decrementing said stored number in said memory means by one unit, and said de-activating pulse is generated for disabling said counter means and said motor driving means and enabling said toggle circuit.

2. An apparatus according to claim 1, wherein said counter means is a programmable counter and said control circuit means further comprises a manual knob connected to said programmable counter for setting said preset number of sequence pulses.

3. An apparatus according to claim 1, wherein said circuit control means further comprises an acoustic indicator for signalling each actuation of said pushbutton.

* * * * *